(12) United States Patent
Cong

(10) Patent No.: US 11,058,690 B2
(45) Date of Patent: Jul. 13, 2021

(54) USE OF CYTOCHROME BC1 COMPLEX INHIBITOR IN PREPARING PHARMACEUTICAL COMPOSITION

(71) Applicant: BEIJING WEILANZHIYUAN MEDICAL TECHNOLOGY CO., LTD., Beijing (CN)

(72) Inventor: Yuwen Cong, Beijing (CN)

(73) Assignee: BEIJING WEILANZHIYUAN MEDICAL TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 16/479,531

(22) PCT Filed: Jan. 22, 2018

(86) PCT No.: PCT/CN2018/073609
§ 371 (c)(1),
(2) Date: Jul. 19, 2019

(87) PCT Pub. No.: WO2018/133862
PCT Pub. Date: Jul. 26, 2018

(65) Prior Publication Data
US 2019/0381055 A1   Dec. 19, 2019

(30) Foreign Application Priority Data

Jan. 22, 2017 (CN) ......................... 201710053062.2
Jan. 25, 2017 (CN) ......................... 201710060825.6
Feb. 9, 2017 (CN) ......................... 201710070661.5

(51) Int. Cl.
*A61K 31/539* (2006.01)
*A61P 29/00* (2006.01)
(Continued)

(52) U.S. Cl.
CPC .......... *A61K 31/539* (2013.01); *A61K 31/122* (2013.01); *A61K 31/155* (2013.01);
(Continued)

(58) Field of Classification Search
CPC ............................. A61P 29/00; A61K 31/122
See application file for complete search history.

(56) References Cited

U.S. PATENT DOCUMENTS

2015/0203445 A1   7/2015   Moore et al.

FOREIGN PATENT DOCUMENTS

CN   103126989 A   6/2013
CN   104334518 A   2/2015

OTHER PUBLICATIONS https://www.google.com/books/edition/Respiration_in_Archaea_and_Bacteria/pkcOBwAAQBAJ?hl=en&gbpv=1: Myers and Kelly, Chapters, vol. 16: Respiration in Archaea and Bacteria, pp. 63-65, (2004). Netherlands: Springer Netherlands. (Year: 2004).*

(Continued)

*Primary Examiner* — Craig D Ricci
*Assistant Examiner* — Janet L Coppins
(74) *Attorney, Agent, or Firm* — Maschoff Brennan; Brent A. Johnson; Yuefen Zhou

(57) ABSTRACT

A use of an inhibitor of the cytochrome bc1 complex for preparing a pharmaceutical composition which treats diseases related to smooth muscle spasms, inflammatory diseases, and relieves pain.

6 Claims, 7 Drawing Sheets

(51) Int. Cl.
*A61P 25/14* (2006.01)
*A61K 31/122* (2006.01)
*A61K 31/155* (2006.01)
*A61K 31/165* (2006.01)
*A61K 31/216* (2006.01)
*A61K 31/22* (2006.01)
*A61K 31/357* (2006.01)
*A61K 31/366* (2006.01)
*A61K 31/40* (2006.01)
*A61K 31/404* (2006.01)
*A61K 31/415* (2006.01)
*A61K 31/4184* (2006.01)
*A61K 31/44* (2006.01)
*A61K 31/4412* (2006.01)
*A61K 31/47* (2006.01)
*A61K 31/473* (2006.01)
*A61K 31/505* (2006.01)

(52) U.S. Cl.
CPC .......... *A61K 31/165* (2013.01); *A61K 31/216* (2013.01); *A61K 31/22* (2013.01); *A61K 31/357* (2013.01); *A61K 31/366* (2013.01); *A61K 31/40* (2013.01); *A61K 31/404* (2013.01); *A61K 31/415* (2013.01); *A61K 31/4184* (2013.01); *A61K 31/44* (2013.01); *A61K 31/4412* (2013.01); *A61K 31/47* (2013.01); *A61K 31/473* (2013.01); *A61K 31/505* (2013.01); *A61P 25/14* (2018.01); *A61P 29/00* (2018.01)

(56) References Cited

OTHER PUBLICATIONS

Sanogo Afr J Tradit Complement Altern Med. (2011) 8(S):90-96 (Year: 2011).*
Yin, "Curative Effect of Omeprazole in the Treatment of 56 Cases of Gastric Ulcer Complicated with Hemorrhage", Contemporary Medicine, 17, (36), Dec. 2011 (with English Abstract).
International Search Report for PCT/CN2018/073609 dated May 23, 2018.

* cited by examiner

USE OF CYTOCHROME BC1 COMPLEX INHIBITOR IN PREPARING PHARMACEUTICAL COMPOSITION

CROSS REFERENCE TO RELATED APPLICATIONS

This application is a national phase of International Patent Application No. PCT/CN2018/073609, filed Jan. 22, 2018, which claims priority to Chinese Patent Application Nos. CN 201710053062.2, filed Jan. 22, 2017; 201710060825.6, filed Jan. 25, 2017; and 201710070661.5, filed Feb. 9, 2017, all of which are incorporated by reference herein by their entirety.

FIELD

The disclosure relates to the bio-pharmaceutical field, particularly, the use of an inhibitor of the cytochrome bc1 complex in medicine. Specifically, this disclosure relates to the use of an inhibitor of the cytochrome bc1 complex for treating a smooth muscle spasm-related disease, treating an inflammatory disease, and relieving a pain.

BACKGROUND

Mitochondrial cytochrome bc1 complex, also known as cytochrome c reductase, or mitochondrial respiratory chain complex III, is an important component of the respiratory electron transport chain of the mitochondria and most bacteria, which catalyzes the transport of electrons from ubiquinone to cytochrome c (cytochrome c2 in bacteria). The cytochrome bc1 complex has two functional quinone-binding sites: one is oxidation site $Q_o$ located on one side of the intermembrane space, close to heme $b_L$; and the other is reduction site $Q_i$ located on one side of the matrix, close to heme $b_H$. Inhibitors of the cytochrome bc1 complex can therefore be divided into two categories: one binds to the $Q_i$ site located on an inner wall of the mitochondrial inner membrane, and this type of inhibitors are called $Q_i$ site inhibitors, such as antimycins and cyazofamids; and the other binds to the $Q_o$ sites located on an outer wall of the mitochondrial inner membrane, and this type of inhibitors are called $Q_o$ site inhibitors, such as methoxyacrylate bactericides, and imidazolinones.

The existing researches on the inhibitors of the cytochrome bc1 complex mainly focus on their bactericidal and insecticidal effects, and there are few reports on the treatment of human diseases using these inhibitors.

SUMMARY

The invention provides a method for treating a smooth muscle spasm-related disease, treating an inflammatory disease and/or relieving a pain by an inhibitor of the cytochrome bc1 complex, use of an inhibitor of the cytochrome bc1 complex in the preparation of a medicament for treating a smooth muscle spasm-related disease, treating an inflammatory disease and/or relieving a pain, and a pharmaceutical composition comprising an inhibitor of the cytochrome bc1 complex.

In some embodiments, the inhibitor of the cytochrome bc1 complex is a Qo site inhibitor of the cytochrome bc1 complex.

In some embodiments, the inhibitor of the cytochrome bc1 complex is a Qi site inhibitor of the cytochrome bc1 complex.

In some embodiments, the inhibitor of the cytochrome bc1 complex is a strobilurin analogue as inhibitor of the cytochrome bc1 complex. In some specific embodiments, the strobilurin analogue as inhibitor of the cytochrome bc1 complex is selected from the group consisting of fluacrypyrim (FAPM), azoxystrobin, trifloxystrobin, kresoximmethyl, pyraclostrobin, picoxystrobin, dimoxystrobin, fluoxastrobin, and prodrugs or pharmaceutically acceptable salts thereof.

In some embodiments, the inhibitor of the cytochrome bc1 complex is a pyridone analogue as inhibitor of the cytochrome bc1 complex. In some specific embodiments, the pyridone analogue as inhibitor of the cytochrome bc1 complex is selected from the group consisting of clopidol, GW844520, GSK932121, and prodrugs or pharmaceutically acceptable salts thereof.

In some embodiments, the inhibitor of the cytochrome bc1 complex is a hydroxynaphthoquinone analogue as inhibitor of the cytochrome bc1 complex. In some specific embodiments, the hydroxynaphthoquinone analogue as inhibitor of the cytochrome bc1 complex is selected from the group consisting of atovaquone, parvaquone, buparvaquone, S-10576, NQ3 (2-OH-3-(2-methyl-trifluorooctyl)-8-methyl-naphthoquinone), and prodrugs or pharmaceutically acceptable salts thereof.

In some embodiments, the inhibitor of the cytochrome bc1 complex is a quinolone analogue as inhibitor of the cytochrome bc1 complex. In some specific embodiments, the quinolone analogue as inhibitor of the cytochrome bc1 complex is selected from the group consisting of RCQ06, Endochin, and Endochin-like quinolones (ELQ), such as ELQ-118, ELQ-120, ELQ-121, ELQ-136, ELQ-233, ELQ-245, ELQ-260, ELQ-271, ELQ-274, ELQ-300, ELQ-314, ELQ-316, ELQ-317, ELQ-319, ELQ-337, ELQ-338, ELQ-351, ELQ-370, ELQ-372, ELQ-380, ELQ-384, ELQ-385, ELQ-388, ELQ-390, ELQ-400, ELQ-404, ELQ-428, P4Q-95 and P4Q-391, and prodrugs or pharmaceutically acceptable salts thereof.

In some embodiments, the inhibitor of the cytochrome bc1 complex is an acridinedione analogue as inhibitor of the cytochrome bc1 complex. In some specific embodiments, the acridinedione analogue as inhibitor of the cytochrome bc1 complex is selected from the group consisting of floxacrine, WR249685, WR243246, and prodrugs or pharmaceutically acceptable salts thereof.

In some embodiments, the inhibitor of the cytochrome bc1 complex is a statin analogue as inhibitor of the cytochrome bc1 complex. In some specific embodiments, the statin analogue as inhibitor of the cytochrome bc1 complex is selected from the group consisting of simvastatin, cerivastatin, rosuvastatin, pravastatin, pitavastatin, mevastatin, lovastatin, fluvastatin, atorvastatin, and prodrugs or pharmaceutically acceptable salts thereof.

In some specific embodiments, the inhibitor of the cytochrome bc1 complex is selected from the group consisting of antimycin A, lansoprazole, lansoprazole sulfide, omeprazole, pentamidine, and prodrugs or pharmaceutically acceptable salts thereof.

In some embodiments, the smooth muscle spasm-related disease is selected from the group consisting of dysmenorrhea; airway spasm-related diseases such as bronchial asthma, asthmatic bronchitis, chronic obstructive pulmonary disease or airway hyperresponsiveness; vasospasm-related diseases such as cerebrovascular spasm, migraine or cluster headache; gastrointestinal spasm-related diseases such as acute gastritis, chronic gastritis, gastric ulcer, duodenal ulcer, acute enteritis, chronic enteritis, Crohn's disease, inflammatory bowel disease, ulcerative colitis or intestinal tuberculosis; hypertension; coronary artery spasm-related diseases such as variant angina pectoris; glaucoma; postoperative intestinal obstruction; frequent urination; fibromyalgia; dyspareunia; irritable bowel syndrome; neck muscle and eyelid spasm; overactive bladder; postoperative ocular inflammation and respiratory distress syndrome.

In some specific embodiments, the inflammatory disease is selected from the group consisting of rheumatoid arthritis, osteoarthritis, osteolysis, tendinitis, synovitis, and inflammatory respiratory diseases such as chronic obstructive pulmonary disease, fibrosis, emphysema or acute respiratory distress syndrome.

In some specific embodiments, the pain is inflammatory pain.

DETAILED DESCRIPTION

Figure 1:
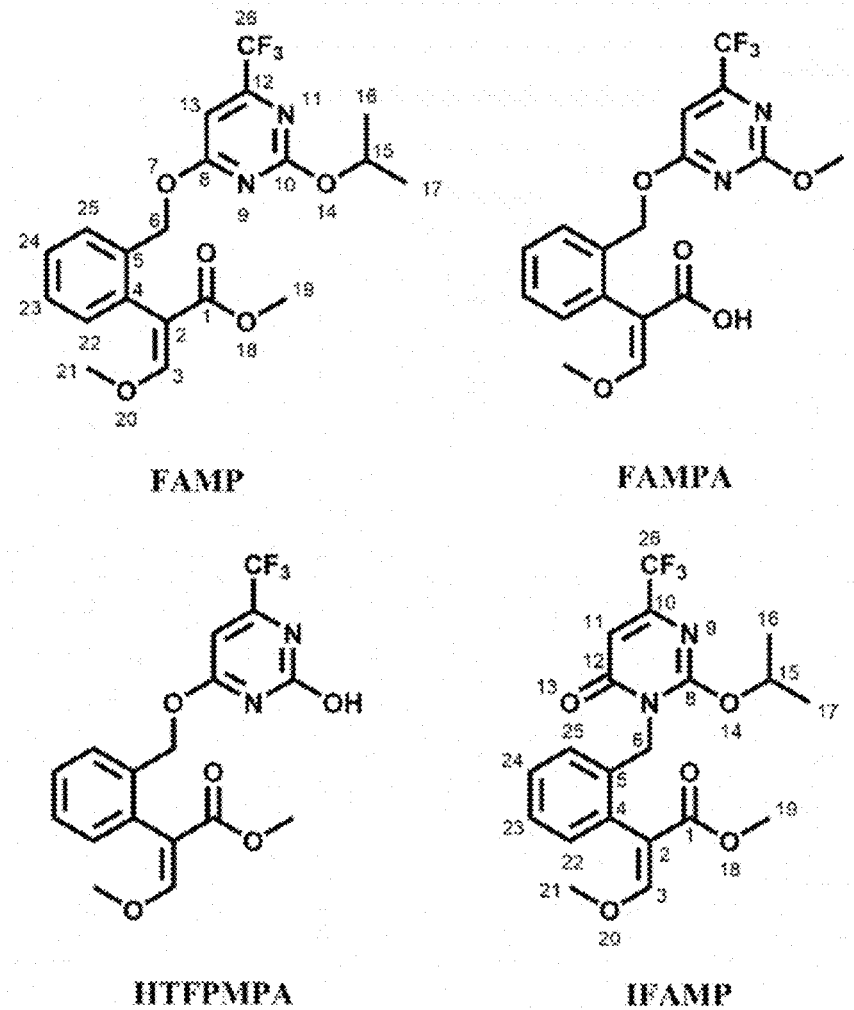
FIG. 1 shows the chemical structure of FAPM and derivatives thereof.

It is known that many diseases with obviously different pathogenesis occurring in different organs are caused by biochemical dysfunction of smooth muscle cells. Proper functioning of smooth muscle cells is the key to avoiding health problems in all organs where smooth muscle cells play an important role.

The inventors surprisingly discovered that the inhibitor of the cytochrome bc1 complex can inhibit smooth muscle contraction in vivo, and thus can be used for treating smooth muscle spasm-related diseases.

Therefore, in the first aspect, the present invention provides a method of treating a smooth muscle spasm-related disease in a subject, comprising administering to the subject a therapeutically effective amount of an inhibitor of the cytochrome bc1 complex.

Without being bound by any theory, the inhibitor of the cytochrome bc1 complex may inhibit smooth muscle contraction by preventing phosphorylation of MLC20. Myosin light chain kinase (MLCK) is a calcium ion and calmodulin dependent protein kinase which specifically phosphorylates the myosin light chain (MLC20) of myosin II. Phosphorylation of MLC20 facilitates interaction between myosin thick filaments and actin thin filaments. MLCK-mediated phosphorylation of MLC20 is necessary to initiate smooth muscle contraction. The inventors surprisingly found that the inhibitor of the cytochrome bc1 complex can prevent phosphorylation of MLC20, thereby treating a smooth muscle spasm-related disease by inhibiting smooth muscle contraction.

As used herein, "smooth muscle" includes, but not limited to, uterine smooth muscle, bladder smooth muscle, iris muscle, genital tract smooth muscle, fallopian tube smooth muscle, bronchial smooth muscle, vascular smooth muscle and gastrointestinal smooth muscle.

As used herein, "smooth muscle spasm-related disease" includes, but not limited to, a disease selected from the following (1)-(8):

(1) gynecological diseases (uterine smooth muscle): dysmenorrhea; premature birth; and preterm premature rupture of membrane;

(2) urinary system diseases (urethral smooth muscle, bladder smooth muscle): benign prostatic hyperplasia; urinary calculi such as kidney calculi and ureteral calculi; overactive bladder; frequent urination; and erectile dysfunction;

(3) digestive system diseases (esophageal smooth muscle, sphincter muscle, gastrointestinal smooth muscle): achalasia of esophagus and cardia; irritable bowel syndrome; sphincter of Oddi dysfunction; gastrointestinal spasmodic abdominal pain, such as gastritis, gastric ulcer, duodenal ulcer, ulcerative colitis, Crohn's disease, and acute and chronic appendicitis; cholelithiasis; acute and chronic cholecystitis; acute and chronic pancreatitis; acute and chronic peritonitis; and intestinal obstruction.

(4) respiratory system diseases (trachea and bronchial smooth muscle): asthma, such as chronic bronchitis asthma, allergic asthma, drug-induced asthma, senile asthma, cough variant asthma, chronic asthma, exercise-induced asthma and childhood asthma; tracheitis; acute and chronic bronchitis; chronic obstructive pulmonary disease; and respiratory distress syndrome;

(5) cardiovascular diseases (vascular smooth muscle): hypertension; portal hypertension; atherosclerosis; angina pectoris, such as variant angina pectoris, unstable angina pectoris, and stable angina pectoris; myocardial infarction; and hypertrophic cardiomyopathy;

(6) cerebral vasospasm-related diseases: ischemic cerebrovascular diseases, such as cerebral infarction, transient ischemic attack, and cerebral thrombosis; vascular dementia; cerebral arteriosclerosis; dizziness; headache; and intractable hiccup;

(7) peripheral vasospasm-related diseases: migraine; intermittent claudication; Raynaud's syndrome; glaucoma; sudden deafness; tinnitus; vertigo; and motion sickness; and (8) others: blepharospasm.

For example, the "smooth muscle spasm-related disease" may be selected from the group consisting of dysmenorrhea; airway spasm-related diseases such as bronchial asthma, asthmatic bronchitis, chronic obstructive pulmonary disease or airway hyperresponsiveness; vasospasm-related diseases such as cerebrovascular spasm, pulmonary hypertension, vascular deafness, migraine or cluster headache; gastrointestinal spasm-related diseases such as cholecystitis, cholangitis, biliary calculus, acute gastritis, chronic gastritis, gastric ulcer, duodenal ulcer, acute enteritis, chronic enteritis, Crohn's disease, inflammatory bowel disease, ulcerative colitis or intestinal tuberculosis; hypertension; coronary artery spasm-related diseases such as variant angina pectoris; cystitis; ureteral calculi; renal colic and glaucoma. In some embodiments, the "smooth muscle spasm-related disease" may also include, for example, postoperative intestinal obstruction, frequent urination, fibromyalgia, dyspareunia, irritable bowel syndrome, neck muscle and eyelid spasm, overactive bladder, postoperative ocular inflammation and respiratory distress syndrome.

For example, the treatment with an inhibitor of the cytochrome bc1 complex may result in significant relaxation of at least some smooth muscle cells, leading to an increase in the arterial diameter of the major artery (e.g., aorta) and the medium-sized artery to lower blood pressure, and an increase in the arterial diameter of the medium-sized artery (e.g., coronary artery) to reduce angina pectoris; a relaxation of pulmonary bronchiole smooth muscle cells to increase the airway diameter, so as to alleviate asthma symptoms; a relaxation of the catheter system of the eye, so as to, for example, increase the diameter of the lacrimal duct to reduce intraocular pressure, thereby reducing the risk of glaucoma and ablepsia; a relaxation of smooth muscle cells of the fallopian tube and uterus to cause the relaxation of muscle tissue, so as to improve fertility and/or alleviate dysmenorrhea symptoms; a relaxation of smooth muscle cells of the bile duct, ureter and urethra to increase the diameter of the catheter, so as to reduce the risk of spasm caused by biliary calculi or kidney calculi; and a relaxation of gastrointestinal smooth muscle to alleviate, for example, spasmodic colic.

In a preferred embodiment, the smooth muscle spasm-related disease is dysmenorrhea. In a further preferred embodiment, the smooth muscle spasm-related disease is primary dysmenorrhea.

In addition, the inventors have surprisingly found that an inhibitor of the cytochrome bc1 complex can significantly inhibit inflammatory symptoms in vivo. For example, it is shown in Example 5 that the inhibitor of the cytochrome bc1 complex can inhibit xylene-induced auricle swelling in mice and carrageenan-induced plantar swelling in rats.

Therefore, in the second aspect, the present invention provides a method of treating an inflammatory disease in a subject, comprising administering to the subject a therapeutically effective amount of an inhibitor of the cytochrome bc1 complex.

Without being bound by any theory, an inhibitor of the cytochrome bc1 complex may inhibit inflammation by inhibiting the production of nitric oxide (NO). NO is an important small molecule substance which regulates life activities, and is synthesized by L-arginine through nitric oxide synthetase (NOS). There are three subtypes of NOS isoenzymes, namely neuronal nitric oxide synthase (nNOS) and endothelial nitric oxide synthase (eNOS) expressed under normal conditions, and inducible nitric oxide synthase (iNOS) induced after injury. Macrophages play an important role in a host defense system, as well as immunity and inflammatory response. Under pathological conditions, the expression of iNOS in macrophages is significantly increased, and a large amount of NO synthesized participates in various acute and chronic inflammatory responses of the body. The inventors surprisingly discovered that an inhibitor of the cytochrome bc1 complex can inhibit the production of nitric oxide by macrophages, and thus can be used to treat inflammatory diseases. For example, it is demonstrated in Example 3 that the inhibitor of the cytochrome bc1 complex can inhibit NO production by mononuclear macrophages in mouse.

Examples of inflammatory diseases that can be treated by the method of the present invention include rheumatoid arthritis, osteoarthritis, osteolysis, tendinitis, synovitis, gout, Alzheimer's disease, glomerulonephritis, pyelonephritis, atherosclerotic diseases, vasculitis, and inflammatory respiratory diseases (such as chronic obstructive pulmonary disease, fibrosis, emphysema, and acute respiratory distress syndrome). Preferably, the inflammatory disease is a non-infectious inflammatory disease.

The inventors also surprisingly found that an inhibitor of the cytochrome bc1 complex has an analgesic effect in vivo. For example, in Example 4 of the present application, administration of the inhibitor of the cytochrome bc1 complex can significantly inhibit the number of writhing of mice caused by acetic acid, diethylstilbestrol and $PGF2\alpha$.

Therefore, in the third aspect, the present invention provides a method of relieving pain in a subject, comprising administering to the subject a therapeutically effective amount of an inhibitor of the cytochrome bc1 complex. In some embodiments, the pain is inflammatory pain, for example, the pain generated after a pain receptor is activated or sensitized when a series of signal transduction pathways are activated via inflammatory mediators released from inflammatory sites where an inflammation occurs in the body.

In some embodiments of various aspects of the present invention, the inhibitor of the cytochrome bc1 complex is a Qo site inhibitor of the cytochrome bc1 complex. In some other embodiments of various aspects of the present invention, the inhibitor of the cytochrome bc1 complex is a Qi site inhibitor of the cytochrome bc1 complex.

In some embodiments, the inhibitor of the cytochrome bc1 complex is a strobilurin analogue as inhibitor of the cytochrome bc1 complex. Examples of the strobilurin analogue as inhibitor of the cytochrome bc1 complex include, but not limited to, fluacrypyrim (FAPM), azoxystrobin, trifloxystrobin, kresoxim-methyl, pyraclostrobin, picoxystrobin, dimoxystrobin, fluoxastrobin, and prodrugs or pharmaceutically acceptable salts thereof.

In some embodiments, the inhibitor of the cytochrome bc1 complex is a pyridone analogue as inhibitor of the cytochrome bc1 complex. Examples of the pyridone analogue as inhibitor of the cytochrome bc1 complex include, but not limited to, clopidol, GW844520, GSK932121, and prodrugs or pharmaceutically acceptable salts thereof.

In some embodiments, the inhibitor of the cytochrome bc1 complex is a hydroxynaphthoquinone analogue as inhibitor of the cytochrome bc1 complex. Examples of the hydroxynaphthoquinone analogue as inhibitor of the cytochrome bc1 complex include, but not limited to, atovaquone, parvaquone, buparvaquone, S-10576, NQ3, and prodrugs or pharmaceutically acceptable salts thereof.

In some embodiments, the inhibitor of the cytochrome bc1 complex is a quinolone analogue as inhibitor of the cytochrome bc1 complex. Examples of the quinolone analogue as inhibitor of the cytochrome bc1 complex include, but not limited to, RCQ06, Endochin, and Endochin-like quinolones (ELQ), such as ELQ-118, ELQ-120, ELQ-121, ELQ-136, ELQ-233, ELQ-245, ELQ-260, ELQ-271, ELQ-274, ELQ-300, ELQ-314, ELQ-316, ELQ-317, ELQ-319, ELQ-337, ELQ-338, ELQ-351, ELQ-370, ELQ-372, ELQ-380, ELQ-384, ELQ-385, ELQ-388, ELQ-390, ELQ-400, ELQ-404, ELQ-428, P4Q-95 and P4Q-391, and prodrugs or pharmaceutically acceptable salts thereof.

In some embodiments, the inhibitor of the cytochrome bc1 complex is an acridinedione analogue as inhibitor of the cytochrome bc1 complex. Examples of the acridinedione analogue as inhibitor of the cytochrome bc1 complex include, but not limited to, floxacrine, WR249685, WR243246, and prodrugs or pharmaceutically acceptable salts thereof.

In some embodiments, the inhibitor of the cytochrome bc1 complex is a statin analogue as inhibitor of the cytochrome bc1 complex. Examples of the statin analogue as inhibitor of the cytochrome bc1 complex include, but not limited to, simvastatin, cerivastatin, rosuvastatin, pravastatin, pitavastatin, mevastatin, lovastatin, fluvastatin, atorvastatin, and prodrugs or pharmaceutically acceptable salts thereof.

In some other embodiments, the inhibitor of the cytochrome bc1 complex may be selected from antimycin A, lansoprazole, lansoprazole sulfide, omeprazole, pentamidine, and prodrugs or pharmaceutically acceptable salts thereof.

The specific inhibitors of the cytochrome bc1 complex described above and other available inhibitors of the cytochrome bc1 complex of the present invention can be found, for example, in Proc Natl Acad Sci USA. 2015 Jan. 20, 112(3): 755-60; Antimicrob Agents Chemother. 2016 Jul. 22, 60(8): 4972-82; Am J Trop Med Hyg. 2015 June, 92(6): 1195-201; PLoS One. 2013 Aug. 12, 8(8): e71726; Nat Commun. 2015 Jul. 9, 6: 7659; Cell Metabolism 22, 399-407, Sep. 1, 2015; Nat Chem Biol. 2015 November, 11(11): 834-6; J. Med. Chem. 2015, 58, 9371-9381; ACS Med. Chem. Lett., 2012, 3 (12), pp 951-951; J. Agric. Food Chem. 2015, 63, 3377-3386; J. Phys. Chem. B 2016, 120, 2701-2708; Mol Biochem Parasitol. 2011 May, 177(1): 12-9; US2015/0203445 A1; and WO 2012070015 A1.

The present invention also covers derivatives of the above-mentioned compounds which have an inhibitory function on the cytochrome bc1 complex.

As used herein, the term "subject" refers to a mammal, preferably a primate, more preferably a human.

In the fourth aspect, the invention further provides use of an inhibitor of the cytochrome bc1 complex in the preparation of a medicament for treating a smooth muscle spasm-related disease, treating an inflammatory disease and/or relieving pain.

In the fifth aspect, the present invention also provides a pharmaceutical composition for treating a smooth muscle spasm-related disease, treating an inflammatory disease and/or relieving pain, comprising an inhibitor of the cytochrome bc1 complex as an active ingredient and a pharmaceutically acceptable carrier.

The pharmaceutical composition of the present invention comprises an effective amount of one or more inhibitors of the cytochrome bc1 complex dissolved or dispersed in a pharmaceutically acceptable carrier. The phrase "pharmaceutically acceptable" refers to molecule entity and composition which do not produce adverse, allergic or other undesirable reactions when administered to an animal (e.g., human) as desired. The preparation of a pharmaceutical composition comprising at least one inhibitor of the cytochrome bc1 complex is known to those skilled in the art according to the present disclosure and is exemplified in "Remington: The Science and Practice of Pharmacy," $21^{st}$ Edition, 2005, which is incorporated herein by reference. In addition, for human administration, it should be understood that the preparation should also meet the standards for sterility, pyrogenicity, overall safety and purity required by the drug approval authority.

As used herein, "pharmaceutically acceptable carrier" includes any and all solvents, dispersion media, antioxidants, salts, coatings, surfactants, preservatives (e.g., methyl or propyl p-hydroxybenzoate, sorbic acid, antibacterial agents, antifungal agents), isotonic agents, solution blockers (e.g., paraffin), adsorbents (e.g., kaolin, bentonite), drug stabilizers (e.g., sodium dodecyl sulfate), gels, binders (e.g., syrup, acacia, gelatin, sorbitol, tragacanth, polyvinylpyrrolidone, carboxymethyl cellulose, alginate), excipients (e.g., lactose, polyethylene glycol), disintegrants (e.g., agar, starch, lactose, calcium phosphate, calcium carbonate, alginic acid, sorbitol, glycine), wetting agents (e.g., hexadecanol, glyceryl monostearate), lubricants, absorption promoters (e.g., quaternary ammonium salt), edible oils (e.g., almond oil, coconut oil, oily ester or propylene glycol), sweeteners, flavoring agents, coloring agents, fillers (e.g., starch, lactose, sucrose, glucose, mannitol, silicic acid), tabletting lubricants (e.g., magnesium stearate, starch, glucose, lactose, chalk), inhalation carriers (e.g., hydrocarbon propellants), buffers or the like and combinations thereof, as understood by those of ordinary skill in the art (see, for example, "Remington: The Science and Practice of Pharmacy", $21^{st}$ Edition, 2005). It is also contemplated to use any conventional carrier other than that incompatible with the active ingredient for the therapeutic or pharmaceutical composition.

In any case, the composition may contain a plurality of antioxidants to retard oxidation of one or more components. Examples of the antioxidants include ascorbic acid, cysteine hydrochloride, sodium sulfite, sodium bisulfite, sodium pyrosulfite, ascorbyl palmitate, butylated hydroxytoluene, butylated hydroxyanisole, lecithin, propyl gallate, and tocopherol. In addition, the prevention of microbial action can be achieved by using preservatives, such as various antibacterial and antifungal agents, including but not limited to parabens (e.g., methyl paraben, propyl paraben), chlorobutanol, phenol, sorbic acid, thimerosal, or combinations thereof.

Pharmaceutically acceptable salts include acid addition salts, such as salts formed with free amino groups of protein components or salts formed with inorganic acids (e.g., hydrochloric acid, hydrobromic acid or phosphoric acid) or organic acids (e.g., acetic acid, oxalic acid, tartaric acid, benzoic acid, lactic acid, phosphonic acid, citric acid, maleic acid, fumaric acid, succinic acid, naphthalenesulfonic acid, clavulanic acid, stearic acid or almond acid). Salts formed with free carboxyl groups may also be derived from inorganic bases (e.g., sodium hydroxide, potassium hydroxide, ammonium hydroxide, calcium hydroxide, magnesium hydroxide or iron hydroxide) or organic bases (e.g., isopropylamine, trimethylamine, histidine or procaine).

In some embodiments where the composition is in a liquid form, the carrier may be a solvent or dispersion medium including, but not limited to, water, ethanol, polyols (e.g., glycerol, propylene glycol, liquid polyethylene glycol), liquids (e.g., triglycerides, vegetable oils, liposomes), and combinations thereof. Appropriate fluidity can be maintained, for example, by using a coating (such as lecithin); by maintaining a desired particle size by dispersing in the carrier (e.g., liquid polyol or lipid); by using a surfactant (e.g., hydroxypropyl cellulose); or combinations of these methods. In many cases, it is preferable to include an isotonic agent (e.g., sugar, sodium chloride, or combination thereof).

The present invention can be administered via any suitable method known to those of ordinary skill in the art (see, for example, Remington: The Science and Practice of Pharmacy, "$21^{st}$ Edition, 2005). The pharmaceutical composition can be administered via intravenous, intramuscular, intraperitoneal, intramedullary, subcutaneous, intra-articular, intrasynovial, intrathecal, oral, local or inhalation route.

When orally administered, the inhibitor of the cytochrome bc1 complex may be in a form of tablet, capsule, sachet, vial, powder, granule, lozenge, reconstitutable powder or liquid preparation. According to needs, a sterile injection solution is prepared by mixing a required amount of the active compound into a suitable solvent containing a plurality of other components mentioned above, and then subjecting to filtration and sterilization. Generally, a dispersion system is prepared by incorporating a plurality of sterile active ingredients into a sterile carrier containing a basic dispersion medium and/or said other components. In the case of sterile powder for preparing a sterile injection solution, suspension or emulsion, a preferred preparation method is vacuum drying or freeze drying technology, which produces a powder containing the active ingredient plus any other desired ingredients from a previously filtered sterile liquid medium. When necessary, the liquid medium should be properly buffered, and a liquid diluent should become isotonic by using sufficient amount of saline or glucose before injection. It is also contemplated to prepare highly concentrated composition for direct injection, where it is conceivable that DMSO used as a solvent will result in extremely rapid permeation, so as to deliver an active medicament in high-concentration to a small area.

As used herein, "therapeutically effective amount" or "therapeutically effective dose" refers to an amount of a substance, compound, material, or composition containing a compound which is at least sufficient to produce a therapeutic effect after administration to a subject. Therefore, it is an amount necessary to prevent, cure, improve, retard or partially retard the symptoms of a disease or disorder.

The actual dosage of the composition of the present invention to be administered to a patient can be determined according to the following physical and physiological factors: weight, sex, severity of symptoms, type of diseases to be treated, previous or current therapeutic intervention, unknown etiological disease of the patient, administration time, excretion rate of specific compounds, and administration route. In any case, the concentration of the active ingredient in the composition and the appropriate dose for an individual subject will be determined by the medical personnel responsible for administration. In some specific embodiments, the inhibitor of the cytochrome bc1 complex is administered at a dose of 1-150 mg/kg body weight, such as 1-100 mg/kg body weight, 1-50 mg/kg body weight, 1-30 mg/kg body weight, 1-20 mg/kg body weight, 1-15 mg/kg body weight, 1-10 mg/kg body weight, 1-5 mg/kg body weight, or 3-5 mg/kg body weight. In some specific embodiments, the inhibitor of the cytochrome bc1 complex or the pharmaceutical composition is administered once a day, twice a day, three times a day, or once every two days, every three days, every four days, every five days, every six days, or every seven days.

In some specific embodiments, prolonged absorption of the injected composition can be achieved by using a delayed absorption agent (e.g., aluminum monostearate, gelatin, or combination thereof) in the composition.

EXAMPLES

The present invention can be further understood by referring to some specific examples given herein, which are only for the purpose of illustrating the present invention and are not intended to limit the scope of the present invention in any way. Obviously, many modifications and changes can be made to the present invention without departing from the essence of the present invention, and therefore, these modifications and changes are also within the scope of the present application.

Example 1. Inhibitory Effect of Inhibitors of the Cytochrome bc1 Complex on the Contraction of Rat Smooth Muscle Experimental Materials and Method
1.1 Laboratory Animals:
1. Wistar rat, female, in weight of 230-270 g, provided by the Laboratory Animal Center of the Academy of Military Medical Sciences, Cat. No. of medical animals: D01-3039.
1.2 Experimental Reagents:
Oxytocin injection (Nanjing Biochemical Pharmaceutical Factory, Cat number 051069); diethylstibestrol (Beijing Yimin Pharmaceutical Co., Ltd., Cat number 0506150); PGF2α, kresoxim-methyl, acetylcholine, azoxystrobin, fluoxastrobin, stigmatellin, myxothiazol and atovaquone, which were all purchased from Sigma (St. Louis, Mo.); trifloxystrobin, pyraclostrobin, picoxystrobin, and dimoxystrobin, which were all purchased from Santa Cruz Biotechnology; and fluacrypyrim (FAPM) and derivatives thereof, which were synthesized in laboratory (Int J Cancer. 2010 Sep. 1; 127(6):1259-70).
1.3 Laboratory Instruments
Pclab Biological Signal Acquisition and Processing System (purchased from Beijing Microsighalstar Technology Development Co., Ltd.); CS502-3C Digital Superthermostat (purchased from Chongqing SD Experiment Instrument Co., Ltd., temperature fluctuation≤0.5° C.); GTS Biosignal Sensor (purchased from Beijing Microsighalstar Technology Development Co., Ltd.); JZ101 Muscle Tension Transducer (Gaobeidian Xinhang Electromechanical Equipment Co., Ltd.).
1.4 Experimental Method
Female healthy Wistar rats weighing 230-270 g were used in the experiment. At 2 days before the experiment, Diethylstilbestrol suspension was injected intraperitoneally once at 0.1 mg/kg, resulting in artificial estrus. The rats were sacrificed by cervical dislocation, and the uterus was removed by laparotomy and immediately placed in a glass plate containing Tyrode's solution. Connective and adipose tissues attached to the uterine wall were carefully peeled off, the uterus was cut open along the mesangial line and laid flat on the bottom of the glass plate, then one side of the uterus was divided into left and right uterine muscle strips by using a surgical blade along the uterine contraction band running along smooth muscle, the two ends of the uterine muscle strip on one side were ligated with wires respectively, and then transferred into a nutrient tube which was aerated with oxygen and filled with 5 ml of Tyrode's solution and preheated to 37.2±0.5° C., with a lower end fixed and an upper end connected with a tension sensor. The materials stood for 20-30 minutes, liquid was changed 2-3 times, then the uterus was given a load of 1 g and kept for 30-60 minutes until the uterus had regular contraction waves, 40 mM KCL solution was provided for 10 minutes, and the function of the uterine muscle strips was evaluated. Then the muscle strips were relaxed and washed 2-3 times with Tyrode's solution, then let stand for 30 minutes; after standing, the uterine muscle strips were given a load of 1 g and kept for 30-60 minutes, and the administration and the observation were carried out after the uterine muscle strips contracted stably (i.e. regular contraction waveforms appear in a microcomputer display screen), the changes of relevant data such as contraction tension, amplitude and area under the contraction curve of the uterine smooth muscle strips were recorded, and the drug given was evaluated. During the experiment, the working temperature of the Tyrode's solution was kept at 37.2±0.5° C., and oxygen was continuously aerated into the nutrient tube with 1-2 bubbles per second. A cumulative dosing method was adopted, and 5 μl was administered each time, from low concentration to high concentration. A final drug concentration refers to the concentration of the drug dissolved in 5 ml Tyrode's solution in a McFarland tube.

1.5 Statistical Treatment

All experimental data were expressed as "x±s", and the SAS software was used to perform single-factor multi-level T test for statistical analysis, and the originpro 7.5 software was used for plotting. Photoshop CS2 software was used for image processing.

2. Experimental Results 2.1 Inhibitory Effect of FAPM and its Derivatives on the Contraction of Rat Smooth Muscle Induced by PGF2α

Figure 2:
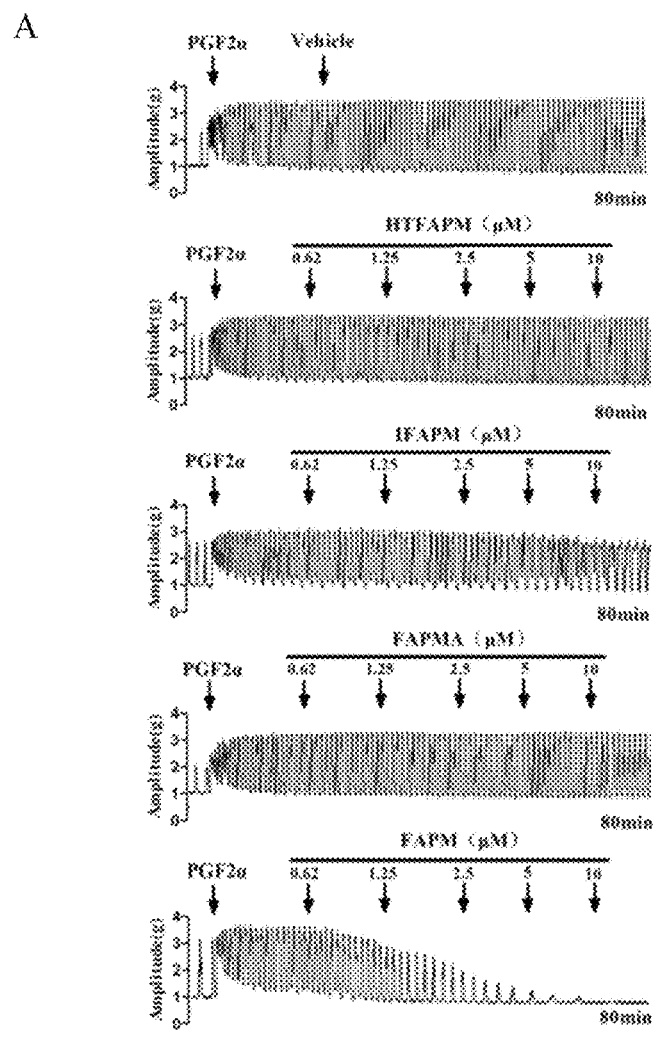
FIG. 2 shows the inhibitory effect of FAPM and derivatives thereof on contraction of rat uterine smooth muscle induced by PGF2α.
Figure 2:
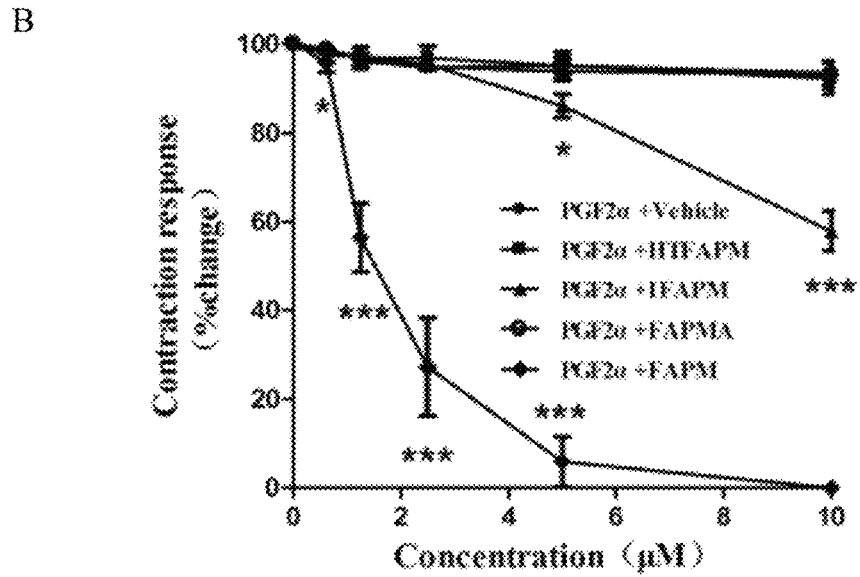

Fluacrypyrim (FAPM), the first strobilurin acaricide developed by BASF SE and Nippon Soda Co., Ltd., is a Qo site inhibitor of the mitochondrial cytochrome bc1 complex. As shown in FIG. 1, HTFAPM, FAPMA and IFAPM are three derivatives of FAPM synthesized by the inventors in the laboratory. As shown in FIG. 2A, under normal circumstances, isolated rat uterine smooth muscle strips underwent occasional autonomic contraction and could spontaneously generate rhythmic contraction. When PGF2α (450 nM) was added to the nutrient tube, the contraction amplitude and frequency of the uterine smooth muscle strips were significantly enhanced. The experiments indicated that FAPM inhibited the amplitude and frequency of PGF2α-inducing rat uterine smooth muscle contraction in a dose-dependent manner. Under the same doses, IFAPM partially inhibited rat uterine smooth muscle contraction induced by PGF2α, while HTFAPM and FAPMA had no inhibitory effect. The area under the smooth muscle contraction curve was calculated before drug intervention and 10 minutes after different doses of drug intervention respectively. A drug dose-effect curve was plotted by taking the area under the smooth muscle contraction curve caused by PGF2α as 100%, to calculate the median effective dose (IC50 value) of the drug for inhibiting uterine smooth muscle contraction. As shown in FIG. 2B, the IC50 values of FAPM and IFAPM were 1.84±0.08 μM and 18.5±3.0 μM respectively. Structure-activity relationship analysis reveals that methoxyacrylate of O14 of FAPM is the key effector group for inhibiting uterine smooth muscle contraction.

2.2 Inhibitory Effect of Strobilurin Fungicides on Rat Smooth Muscle Contraction Induced by PGF2α

Figure 3:
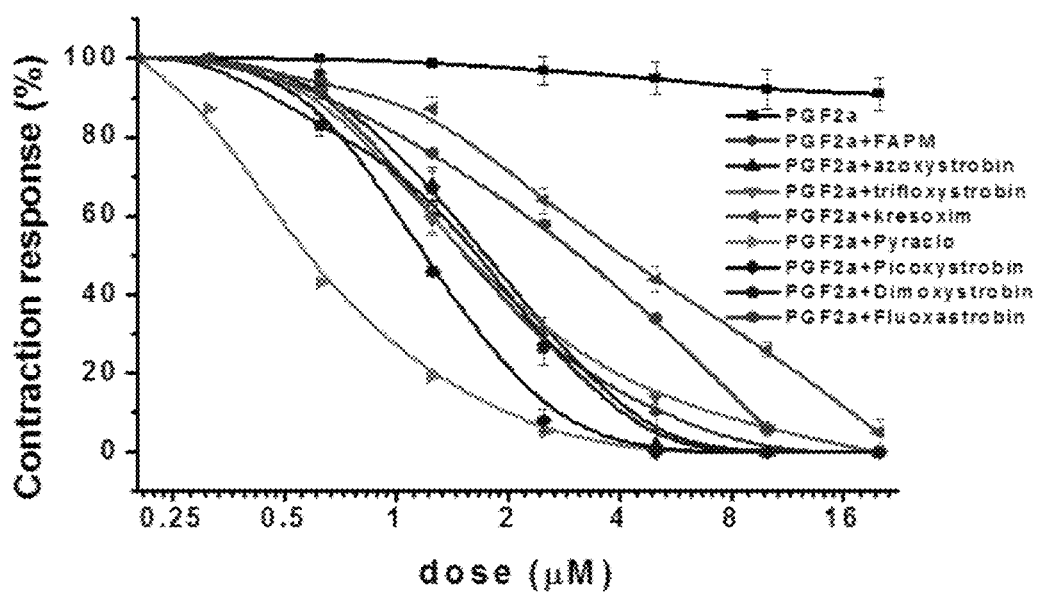
FIG. 3 shows the inhibitory effect of a $Q_o$ site inhibitor of the cytochrome bc1 complex on contraction of rat uterine smooth muscle induced by PGF2α.

Herein, on an experimental model of rat uterine smooth muscle contraction induced by PGF2α, the inhibitory effects of various strobilurin fungicides such as azoxystrobin, trifloxystrobin, kresoxim-methyl, fluoxastrobin, pyraclostrobin, picoxystrobin and dimoxystrobin on uterine smooth muscle contraction were systematically compared. As shown in FIG. 3 and Table 1, these compounds inhibited rat uterine smooth muscle contraction induced by PGF2α in a dose-dependent manner, with IC50 values of between 1.05 and 4.08 μM, which is equivalent to FAPM. Stigmatellin and myxothiazol are the strongest respiratory inhibitors of the cytochrome bc1 complex as reported and the most commonly used small molecule compound probes for studying a cytochrome bc1 complex. It is found that both had the strongest inhibitory effect on rat uterine smooth muscle contraction induced by PGF2α, with IC50 values at a nanomolar level.

TABLE 1

Inhibitory effect of the inhibitors of the cytochrome bc1 complex on rat uterine smooth muscle contraction induced by PGF2α

| Inhibitor | IC 50 (μM) |
| --- | --- |
| FAPM | 1.69 ± 0.16 |
| azoxystrobin | 1.70 ± 0.12 |
| trifloxystrobin | 1.77 ± 0.05 |
| kresoxim-methyl | 4.08 ± 0.29 |
| Pyraclostrobin | 1.05 ± 0.01 |
| Picoxystrobin | 1.20 ± 0.02 |
| Dimoxystrobin | 1.65 ± 0.12 |
| Fluoxastrobin | 2.63 ± 0.30 |
| Stigmatellin | 89.9 nM |
| Myxothiazol | 214.7 nM |

Figure 4:
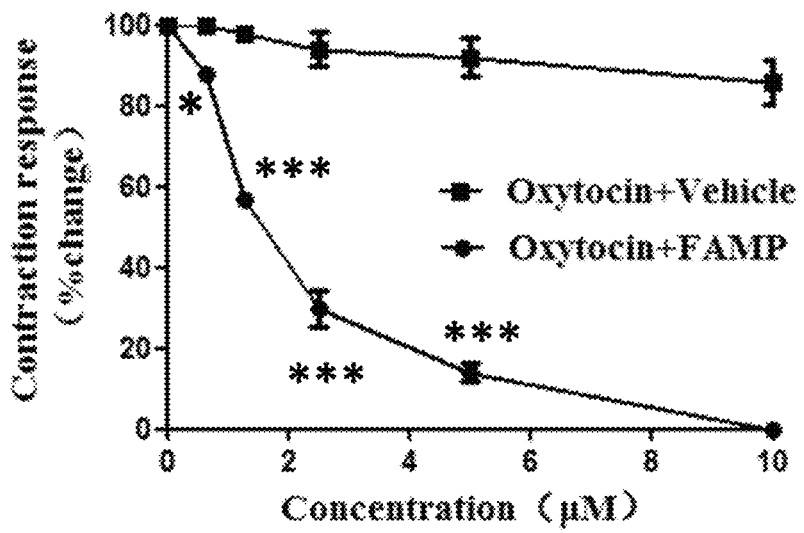
FIG. 4 shows the inhibitory effect of FAPM on contraction of rat uterine smooth muscle induced by rat oxytocin.
Figure 5:
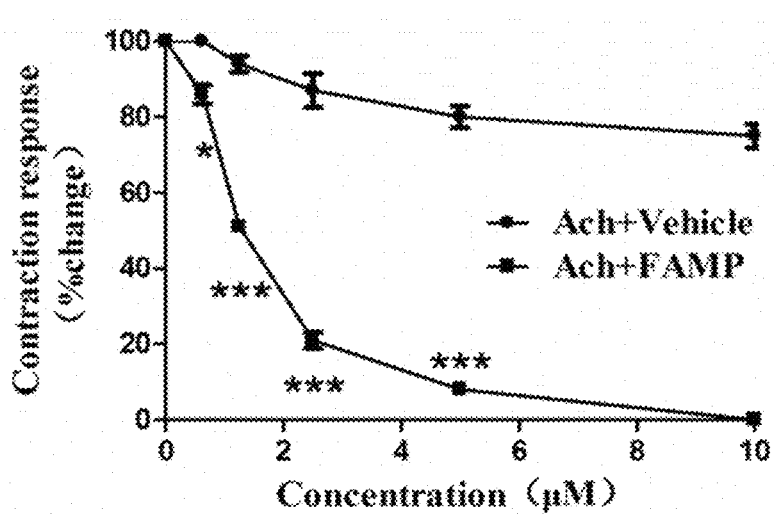
FIG. 5 shows the inhibitory effect of FAPM on contraction of rat uterine smooth muscle induced by acetylcholine.
Figure 6:
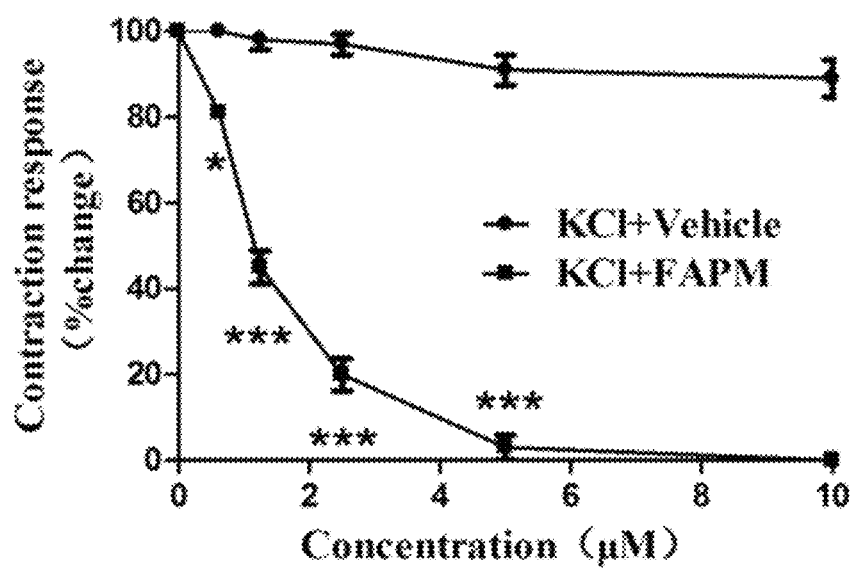
FIG. 6 shows the inhibitory effect of FAPM on contraction of rat uterine smooth muscle induced by potassium chloride.

2.3 Inhibitory Effect of FAPM on the Contraction of Rat Smooth Muscle Induced by Oxytocin, Acetylcholine and Potassium Chloride Oxytocin is an excitant for uterine smooth muscle, which causes rhythmic contraction of uterine smooth muscle by activating an oxytocin receptor. Acetylcholine is a neurotransmitter, which can activate a smooth muscle M-type choline receptor to cause rhythmic contraction of uterine smooth muscle. Potassium chloride can depolarize a smooth muscle cell membrane, high-concentration of potassium chloride (40 mM) can cause tetanic contraction of uterine smooth muscle, and low-concentration of potassium chloride (16 mM) can cause rhythmic contraction of uterine smooth muscle. As shown in FIGS. 4-6, FAPM inhibited uterine smooth muscle contraction induced by oxytocin (1 mU/ml), acetylcholine (0.25 μM) and potassium chloride (16 mM) in a dose-dependent manner, with IC50 values of 1.6±0.08 μM, 1.36±0.04 μM and 1.21±0.07 μM respectively.

2.4 Inhibitory Effect of Atovaquone on the Contraction of Rat Smooth Muscle Induced by PGF2α

Figure 7:
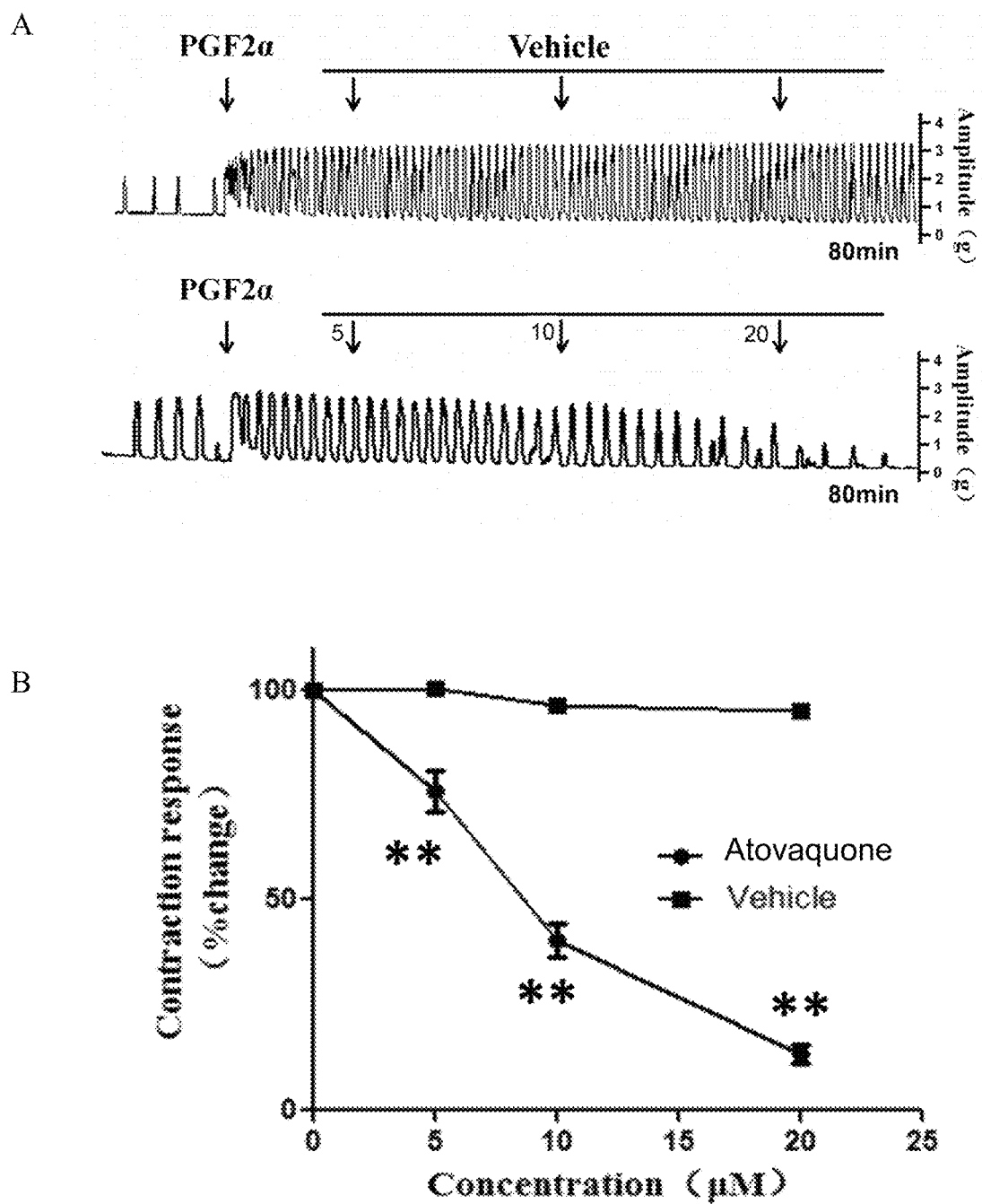
FIG. 7 shows the inhibitory effect of atovaquone on contraction of rat uterine smooth muscle induced by PGF2α. IC50=8.44±0.7 µM.

Atovaquone is hydroxy 1,4-naphthoquinoline, a homolog of coenzyme Q, and has a broad-spectrum antiprotozoal activity. U.S. Food and Drug Administration (FDA) approved atovaquone in 2011 for the treatment of *Plasmodium, Pneumocystis carinii* pneumonia (PCP), *Toxoplasma gondii* and other infections; and Infectious Diseases Society of America (IDSA) guidelines recommended atorvastatin for the treatment of toxoplasmosis in 2006. Atovaquinone can directly bind to a protozoan cytochrome bc1 complex, and the inhibition of the activity of the cytochrome bc1 complex is its molecular pharmacological mechanism to exert the broad-spectrum antiprotozoal efficacy (Siregar J E, Kurisu G, Kobayashi T, et al. Direct evidence for the atovaquone action on the *Plasmodium* cytochrome bc1 complex. Parasitol Int. 2015 June; 64(3):295-300). Based on this, the inhibitory effect of atorvastatin on the contraction of rat uterine smooth muscle induced by PGF2α was observed. It is found that atorvastatin can inhibit the contraction of rat uterine smooth muscle induced by PGF2α in a dose-dependent manner, with IC50 value of 8.44±0.7 μM (FIG. 7).

Example 2. Inhibitory Effect of FAPM as the Inhibitor of the Cytochrome bc1 Complex on the Phosphorylation of MLC20 in Rat Smooth Muscle Cells 1. Experimental Materials and Method 1.1. Laboratory Animals:

Wistar rat, female, weight 230-270 g, provided by the Laboratory Animal Center of the Academy of Military Medical Sciences, Cat. No. of medical animals: D01-3039.

1.2. Experimental Reagents:

WB 2×SDS loading buffer, 5×Tris-glycine electrophoresis buffer, electrotransfer buffer and separation gel buffer, were all self-prepared (see Solution Preparation), wherein the reagents and X-ray photosensitive films were all purchased from Beijing Chemical Works; and the monoclonal antibody against phospho-myosin light chain-2 (ser19), horseradish peroxidase labeled secondary antibody and horseradish peroxidase chromogenic substrate LumiGLO® substrate, were all purchased from Cell Signaling Technology.

1.3. Laboratory Instruments:

DNM-9602G microplate reader, purchased from Beijing Perlong New Technology Co., Ltd.; and stable voltage and current power supply, protein electrophoresis instruments, protein electrotransfer device and protein molecular weight marker, purchased from New England Biotech.

1.4. Culturing of Rat Uterine Smooth Muscle Cells In Vitro:

A tissue mass culture method was adopted: rats treated with diethylstilbestrol were sacrificed through dislocation and soak in 75% alcohol for disinfection, open the abdominal cavity under an aseptic condition, separate the uterus, transfer it to a plate, cut open the uterus to remove the outer membrane of the uterus, gently scrape off the inner membrane of the uterus with a blade, gently peel off the outer membrane of the uterus with a tweezer, cut the intact smooth muscle into small pieces of less than 1×1×1 mm$^3$, uniformly stick them to the wall of a culture bottle, add a culture solution with the bottom up, gently turn over after culture at 5% $CO_2$ and 37° C. for 3-4 hours, and soak in an RPMI-1640 culture solution (containing 20% calf bovine serum) for about one week until the cells can be connected into pieces to form monolayer cultured cells. At this time, the culture solution in the bottle was poured out, the tissue masses in the bottle were washed twice with PBS and removed, and a proper amount of 0.25% trypsin was added. Calf bovine serum was added to stop the reaction when most cells contracted and became round under microscope, the liquid was poured out, and the cells were washed twice with PBS and added with a proper amount of RPMI-1640, and the eluted cells were gently washed with a pipette to prepare a cell suspension for later use.

1.5. Extraction of Whole Cell Protein:

The cells were adjusted to a concentration of $10^5$/ml, and inoculated into a 6-well plate at a density of $4×10^5$/well, after adherent culturing overnight, was deprived of serum for 24 hours, and then pretreated with FAPM of different concentrations. The cells were collected 5 minutes after $PGF_{2α}$ stimulation, washed 3 times with ice-cold PBS, and lysed with a 2×SDS loading buffer. The cell lysate was collected and boiled for 10 min, then centrifuged at 12000 r/min for 5 minutes. The supernatant was collected and subpackaged and stored at −80° C. for later use.

1.6. Immunoblotting Detection (Western Blotting Hybridization):

The subpackaged cell lysate was thawed at room temperature and then subjected to SDS-PAGE gel electrophoresis. The sample was carefully added into comb holes with a micro syringe, the voltage was stabilized at 100 V until the bromophenol blue band ran outside the separation gel, and then the voltage was adjusted to 200 V; after electrophoresis, membrane transfer was performed under a stable current of 160 mA 1 h in ice bath, so that the protein was transferred to a nitrocellulose membrane; and the membrane was transferred to a plate, blocked for 1 h with 5% skim milk at room temperature, washed 3 times with TBS/T, 5 min for each, incubated overnight with a primary antibody diluent at appropriate proportion, washed 4 times with TBS/T, 5 min for each, the next day, incubated for another 1 h with a secondary antibody diluent at appropriate proportion, washed 4 times with TBS/T, 5 min for each, incubated in dark for 1 min with LumiGLO® substrate. The development of X-ray film was carried out in dark room. The membrane can be re-labelled with other antibodies if necessary, the membrane can be incubated with a clearing buffer (see Solution Preparation) at 65° C. for 30 min, after clearing, the membrane can be washed with TBS/T, and the antibody can be labelled after blocking.

1.7. Statistical Treatment

All experimental data were expressed as "x±s", SAS software was used to perform single-factor multi-level T test for statistical analysis, and originpro7.5 software was used for plotting. Photoshop CS2 software was used for image processing.

2. Results

Figure 8:
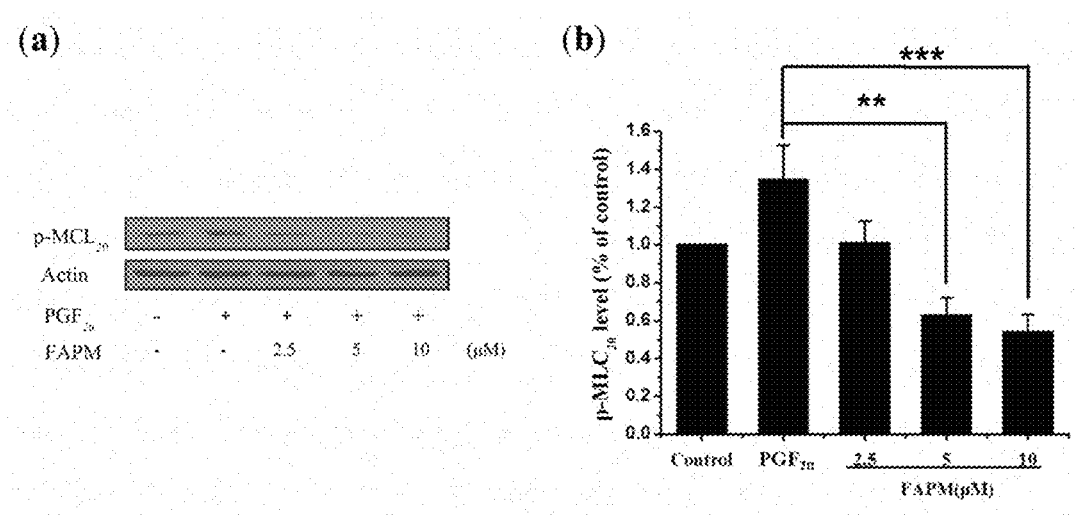
FIG. 8 shows the inhibitory effect of FAPM on phosphorylation of MLC20 in rat smooth muscle cells induced by PGF2α.

As shown in FIG. 8, PGF2α stimulation significantly enhanced the phosphorylation of MLC20 in rat uterine smooth muscle cells. After pretreatment with FAPM of different concentrations in advance, the phosphorylation degree of MLC20 was significantly reduced. Gray analysis showed that 5 μM and 10 μM of FAPM significantly inhibited the phosphorylation of MLC20 in rat uterine smooth muscle cells induced by PGF2α. This result indicated that the inhibitor of the cytochrome bc1 complex such as FAPM may inhibit smooth muscle contraction by preventing MLC20 phosphorylation.

Example 3. Inhibitory Effect of Inhibitors of the Cytochrome bc1 Complex on Nitric Oxide Production by Macrophages 1. Materials and Method 1.1 Cell Strain;

Mouse mononuclear macrophage RAW 264.7 was purchased from Xiehe Cell Bank.

1.2 Reagents and instruments

Lipopolysaccharide (LPS) purchased from Sigma; RPMI1640 medium, penicillin, streptomycin and fetal bovine serum purchased from Invitrogen; nitric oxide test kit purchased from Beyotime Biotechnology; and NM-9602G microplate reader purchased from Beijing Perlong New Technology Co., Ltd.

1.3 Cell Culture

Mouse mononuclear macrophages were cultured in the RPMI1640 medium containing 10% fetal bovine serum, 100 μg·mL$^{-1}$ streptomycin, and 100 units·mL$^{-1}$ penicillin, incubated in a constant-temperature incubator at 37° C. and 5% $CO_2$, and passaged the next day.

1.4 Determination of NO Released

The content of NO in the sample was determined by Griess assay. RAW 264.7 cells were prepared into a single cell suspension containing $5×10^5$ cells/mL and inoculated into a 96-well cell culture plate (200 μL/well). After incubation for 12 h in an incubator at 37° C. and 5% $CO_2$, test samples of different concentrations were added to each well, and LPS (in a final concentration of 1 μg·mL$^{-1}$) was added after incubation for 30 minutes. An LPS and a blank control groups were set up with 3 repeated wells for each sample. After incubation in an incubator for 24 h, 100 μL supernatant of the culture solution was aspirated into an enzyme-labeled plate, an equal volume of Griess reagent was added, and the absorbance at 540 nm was measured after 10 min of reaction at room temperature. The inhibition rate was calculated as follows: inhibition rate=$[OD]_{LPS}-[OD]_{LPS+sample}/[OD]_{LPS}-[OD]_{blank} \times 100\%$.

2. Results

Mouse peritoneal macrophage cell line RAW264.7 is one of the commonly used cell models for inflammation study. LPS was used to stimulate RAW264.7 cells to produce NO, and the inhibitory effects of various inhibitors of the cytochrome bc1 complex on NO production by macrophages were observed. As shown in Table 2, the inhibitors of the cytochrome bc1 complex, azoxystrobin, trifloxystrobin, kresoxim-methyl and FAPM all significantly inhibited NO production, with IC50 of 1.89±0.35 μM, 0.64±0.21 μM, 2.77±0.69 μM, and 3.80 μM respectively. The maximum inhibition rates were all above 80%, and the effective concentration was equivalent to that for inhibition of uterine smooth muscle contraction. Stigmatellin and myxothiazol have the strongest inhibitory activity on uterine smooth muscle contraction, and their IC50 values for inhibiting NO production are also the lowest, 6.24±1.15 nM and 2.8 nM respectively, and the maximum inhibitory rates are 88.3±3.9% and 95% respectively.

TABLE 2

Inhibitory Effect of Inhibitors of the cytochrome bc1 complex on Nitric Oxide Production by Macrophages

| Inhibitor | IC 50 (μM) | Maximum inhibition rate |
| --- | --- | --- |
| azoxystrobin | 1.89 ± 0.35 μM | 86.7 ± 4.3 |
| trifloxystrobin | 0.64 ± 0.21 μM | 90.7 ± 2.9 |
| kresoxim-methyl | 2.77 ± 0.69 μM | 88.7 ± 5.6 |
| FAPM | 3.80 μM | 80 |
| Stigmatellin | 6.24 ± 1.15 nM | 88.3 ± 3.9 |
| Myxothiazol | 2.8 nM | 95 |

Example 4. Study on Analgesic Effect of Inhibitors of Cytochrome bc1 Complex In Vivo 1. Materials and Method 1.1 Laboratory Animals:

Clean Kunming female and male mice, weight 22-28 g, provided by the Laboratory Animal Center of the Academy of Military Medical Sciences, Cat. No. of medical animals: D01-3039.

1.2 Experimental Drugs and Reagents

Oxytocin injection (Nanjing Biochemical Pharmaceutical Factory, cat. Number: 051069); diethylstibestrol (Beijing Yimin Pharmaceutical Co., Ltd., cat. Number: 0506150); indomethacin, PGF2α, kresoxim-methyl and azoxystrobin purchased from Sigma (St. Louis, Mo.); trifloxystrobin, picoxystrobin and dimoxystrobin purchased from Santa Cruz Biotechnology; and FAPM synthesized by the inventors in the laboratory (Int J Cancer. 2010 Sep. 1; 127(6): 1259-70).

1.3 Acetic Acid Writhing Test on Mice

With reference to the acetic acid writhing test on mice in Xu Shuyun's "Pharmacological Experimental Methodology", a pain model of peritonitis in mice was reproduced. Adult healthy Kunming male mice were randomly grouped, 6-10 mice in one group. One hour before the experiment, mice were given different kinds and dosages of inhibitors of the cytochrome bc1 complex intraperitoneally or intragastrically, indometacin (50 mg/kg) was injected intraperitoneally as positive control, then 0.6% glacial acetic acid was injected intraperitoneally at 0.1 ml/10 g, and the writhe starting time (reaction latency) and the number of writhing times within 30 min were observed and recorded.

1.4 Establishment of Mouse Dysmenorrhea Model

A mouse dysmenorrhea model was established with reference to Yang L., Cao Z., Yu B. & Chai C. An in vivo mouse model of primary dysmenorrhea. Exp Anim. 2015, August 64, 295-303. Adult healthy Kunming female mice were randomly grouped, 10 mice in each group. Experimental mice were intragastrically given diethylstilbestrol 0.2 mg daily for 12 days. Different kinds and dosages of the inhibitors of the cytochrome bc1 complex were given intraperitoneally or intragastrically 30 min after the last administration. Indometacin (50 mg/kg) was injected intraperitoneally as positive control, PGF2α (1.3 mg/kg) or oxytocin (20 U/kg) was injected intraperitoneally 1 h later, and the writhe starting time (reaction latency) and the number of writhing times within 30 min were observed and recorded.

1.5 Statistical Treatment

All experimental data were expressed as "x±s", and SAS software was used to conduct single-factor multi-level T test for statistical analysis.

2. Results 2.1 Inhibitory Effect of the Inhibitors of the Cytochrome bc1 Complex on Acetic Acid-Induced Writhing in Mice Pain is an unpleasant feeling and emotional experience caused by acute or potential tissue injury. Pain models obtained by chemical stimulation such as glacial acetic acid, which is currently the most studied and widely used pain models. These inflammatory stimulation drugs cause acute inflammatory pain through neutrophil chemotaxis and mediate macrophage infiltration to cause persistent pain. Mouse acetic acid writhing test is suitable for screening non-narcotic analgesics, and is especially a sensitive and simple method for screening analgesic effects of steroidal anti-inflammatory drugs. As shown in Tables 3-6, within 30 minutes after intraperitoneal injection of glacial acetic acid (0.6%, 0.1 ml/10 g), the mice writhed about 40 times with a latency of 2-3 minutes. Intraperitoneal injection of the inhibitors of the cytochrome bc1 complex, FAPM (50, 100 and 200 mg/Kg) and trifloxystrobin (50, 100 and 200 mg/Kg) or intragastric administration of azoxystrobin (50, 100, 200 and 400 mg/Kg) 1 hour before the experiment, inhibited the number of writhing of the mice in a dose-dependent manner. Compared with the control group, the writhe starting time (reaction latency) of the FAPM group and trifloxystrobin group was significantly prolonged and there was a dose effect, while the writhe starting time of the azoxystrobin group was not significantly prolonged. FAPM, trifloxystrobin and azoxystrobin at 100 mg/Kg were equivalent to indomethacin at 50 mg/Kg in terms of curative effect. At the dosage of 200 mg/Kg, the inhibitory effects of the inhibitors of the cytochrome bc1 complex, dimoxystrobin, kresoxim-methyl and picoxystrobin, which were intragastrically administrated, on acetic acid-induced writhing in mice were compared. It was found that these three inhibitors obviously inhibited the number of writhing times of the mice, but the writhe starting time was not prolonged.

TABLE 3

Inhibitory Effect of Intraperitoneal Administration of FAPM on Acetic Acid-induced Writhing in Mice

| | Dosage | Number of animals | Number of writhing times | Writhe starting time |
| --- | --- | --- | --- | --- |
| Solvent | 0.2 ml | 10 | 38.5 ± 3.8 | 2.4 ± 0.9 |
| control group | 50 mg/Kg | 10 | 15.8 ± 3.9** | 4.6 ± 0.8** |
| Indomethacin | 50 mg/Kg | 10 | 25.3 ± 4.7** | 3.4 ± 1.1** |

TABLE 3-continued

Inhibitory Effect of Intraperitoneal Administration of FAPM on Acetic Acid-induced Writhing in Mice

| | Dosage | Number of animals | Number of writhing times | Writhe starting time |
|---|---|---|---|---|
| group | 100 mg/Kg | 10 | 17.6 ± 3.5** | 4.6 ± 1.5** |
| FAPM | 200 mg/Kg | 10 | 2.4 ± 2.2** | 11.9 ± 2.6** |

Compare with transplant control group **P < 0.01.

TABLE 4

Inhibitory Effect of Intraperitoneal Administration of Trifloxystrobin on Acetic Acid-induced Writhing in Mice

| | Dosage | Number of animals | Number of writhing times | Writhe starting time |
|---|---|---|---|---|
| Solvent | 0.2 ml | 6 | 42.0 ± 5.1 | 2.3 ± 0.5 |
| control group | 50 mg/Kg | 6 | 22.3 ± 1.2** | 3.3 ± 0.5* |
| Trifloxystrobin | 100 mg/Kg | 6 | 14.0 ± 1.7** | 4.3 ± 1.6** |
| | 200 mg/Kg | 6 | 4.0 ± 2.3** | 8.5 ± 2.4** |

Compare with transplant control group P < 0.05; P < 0.01.

TABLE 5

Inhibitory Effect of Intragastric Administration of Azoxystrobin on Acetic Acid-induced Writhing in Mice

| | Dosage | Number of animals | Number of writhing times | Writhe starting time |
|---|---|---|---|---|
| Solvent | 0.2 ml | 10 | 41.3 ± 3.8 | 2.5 ± 1.0 |
| control group | 50 mg/Kg | 10 | 24.8 ± 4.8** | 3.4 ± 1.0 |
| Indomethacin | 50 mg/Kg | 10 | 31.9 ± 3.1** | 3.2 ± 1.1 |
| group | 100 mg/Kg | 10 | 24.9 ± 4.6** | 3.4 ± 1.8 |
| Azoxystrobin | 200 mg/Kg | 10 | 21.6 ± 3.5** | 3.7 ± 1.5 |
| | 400 mg/Kg | 10 | 12.4 ± 4.2** | 3.4 ± 1.2 |

Compare with transplant control group **P < 0.01.

TABLE 6

Inhibitory Effect of Intragastric Administration of Dimoxystrobin, Kresoxim-methyl and Picoxystrobin on Acetic Acid-induced Writhing in Mice

| | Dosage | Number of animals | Number of writhing times | Writhe starting time |
|---|---|---|---|---|
| Solvent control group | 0.2 ml | 10 | 41.3 ± 3.8 | 3.1 ± 0.7 |
| Dimoxystrobin | 200 mg/Kg | 10 | 31.5 ± 4.7** | 3.3 ± 0.5 |
| Kresoxim-methyl | 200 mg/Kg | 10 | 33.0 ± 2.9** | 3.4 ± 1.0 |
| Picoxystrobin | 200 mg/Kg | 10 | 29.3 ± 4.7** | 3.3 ± 1.0 |

Compare with transplant control group **P < 0.01.

2.2 Analgesic Effects of Inhibitors of the Cytochrome bc1 Complex FAPM and Azoxystrobin on Dysmenorrhea Model Mice Dysmenorrhea is one of the most common gynecologic symptoms and is divided into two types, primary and secondary dysmenorrhea. Primary dysmenorrhea refers to dysmenorrhea without organic lesions in reproductive organs, accounting for more than 90% of dysmenorrhea; and secondary dysmenorrhea refers to dysmenorrhea caused by pelvic cavity organic diseases. The occurrence of primary dysmenorrhea is mainly related to the increase of prostaglandin content in endometrium during menstruation. The increase of PGF2α content is the main cause of dysmenorrhea. Based on the pathophysiological mechanism of dysmenorrhea and the references, a mouse dysmenorrhea model induced by a two-step method including diethylstilbestrol sensitization and PGF2α pain inducing was established.

As shown in Table 7 and Table 8, after sensitization with diethylstilbestrol, within 30 minutes after intraperitoneal injection of PGF2α (1.3 mg/kg), the number of writhing times of the mice reached about 20, with a latency of 1-2 minutes. Intraperitoneal injection of the inhibitor of the cytochrome bc1 complex FAPM (50, 100 and 200 mg/Kg) or intragastric administration of azoxystrobin (50, 100 and 200 mg/Kg) one hour before the experiment, inhibited the number of writhing times of the mice in a dose-dependent manner, and there were statistical differences between each dosage group and the control group. Except for the 200 mg/Kg FAPM group where the writhe starting time was significantly prolonged, the writhe starting time of other groups was not significantly different from that of the control group. FAPM and azoxystrobin at 50 mg/Kg were equivalent to indomethacin at 50 mg/Kg in terms of curative effect.

Oxytocin is a stimulant for uterine smooth muscle. As shown in FIG. 9, in a mouse dysmenorrhea model induced by a two-step method including diethylstilbestrol sensitization and oxytocin pain inducing, the number of writhing times of the mice was nearly 40. Intragastric administration of azoxystrobin (50, 100 and 200 mg/Kg) inhibited the number of writhing times of the mice in a dose-dependent manner, and there were statistical differences between each dose group and the control group. In this model, 50 mg/Kg of azoxystrobin was equivalent to 50 mg/Kg of indomethacin in terms of curative effect.

TABLE 7

Analgesic Effect of Intraperitoneal Administration of FAPM on PGF2a-induced Dysmenorrhea in Mice

| | Dosage | Number of animals | Number of writhing times | Writhe starting time |
|---|---|---|---|---|
| Solvent | 0.2 ml | 10 | 20.0 ± 2.1 | 1.53 ± 0.54 |
| control group | 50 mg/Kg | 10 | 15.0 ± 2.1** | 1.89 ± 0.6 |
| Indomethacin | 50 mg/Kg | 10 | 18.3 ± 3.3 | 1.24 ± 0.66 |
| group | 100 mg/Kg | 10 | 12.5 ± 1.7** | 1.43 ± 0.73 |
| FAPM | 200 mg/Kg | 10 | 5.8 ± 1.2** | 2.15 ± 0.34** |

Compare with transplant control group **P < 0.01.

TABLE 8

Analgesic Effect of Intragastric Administration of Azoxystrobin on PGF2a-induced Dysmenorrhea in Mice

| | Dosage | Number of animals | Number of writhing times | Writhe starting time |
|---|---|---|---|---|
| Solvent | 0.2 ml | 10 | 22.6 ± 2.7 | 2.0 ± 0.8 |
| control group | 50 mg/Kg | 10 | 16.8 ± 2.5** | 2.1 ± 1.2 |
| Indomethacin | 50 mg/Kg | 10 | 17.7 ± 1.9** | 2.1 ± 1.0 |
| group | 100 mg/Kg | 10 | 12.8 ± 2.4** | 2.0 ± 1.1 |
| Azoxystrobin | 200 mg/Kg | 10 | 10.3 ± 1.3** | 2.2 ± 0.8 |

Compare with transplant control group **P < 0.01.

TABLE 9

Analgesic Effect of Intragastric Administration of Azoxystrobin on Oxytocin-induced Dysmenorrhea in Mice

| | Dosage | Number of animals | Number of writhing times | Writhe starting time |
|---|---|---|---|---|
| Solvent control group | 0.2 ml | 10 | 36.7 ± 3.6 | 3.2 ± 0.9 |
| Indomethacin group | 50 mg/Kg | 10 | 14.7 ± 1.4** | 3.5 ± 1.0 |
| | 50 mg/Kg | 10 | 24.2 ± 4.1** | 3.3 ± 1.5 |
| | 100 mg/Kg | 10 | 14.2 ± 2.2** | 3.9 ± 1.5 |
| Azoxystrobin | 200 mg/Kg | 10 | 7.6 ± 1.9** | 3.3 ± 1.3 |

Compare with transplant control group **$P < 0.01$.

Example 5. Study on Anti-Inflammatory Effect of the Inhibitor of the Cytochrome bc1 Complex FAPM In Vivo 1. Materials and Method 1.1 Laboratory Animals:

Clean Kunming female mice, weight 22-28 g, and SD rats, weight 120-140 g, provided by the Laboratory Animal Center of the Academy of Military Medical Sciences, Cat. No. of medical animals: D01-3039.

1.2 Experimental Drugs and Reagents

Indomethacin, dexamethasone and carrageenan xylene purchased from Sigma (St. Louis, Mo.); and FAPM synthesized by the inventors in the laboratory (Int J Cancer. 2010 Sep. 1; 127(6): 1259-70).

1.3 Xylene-Induced Mouse Ear Swelling Test

Fifty healthy adult male mice were randomly divided into 5 groups. The experimental mice were injected intraperitoneally with different doses of FAPM (50, 100 and 200 mg/kg) once respectively. A control group was injected with the same amount of solvent, and indomethacin (50 mg/kg) was injected intraperitoneally as a positive control. One hour after administration, 20 µL of xylene was evenly applied to both sides of the right ear of mouse, and xylene was not applied to the left ear as self control. One hour later, the two ears were cut off, and two ear pieces were removed from the same parts of the two ears with a 6 mm hole punch. The two ear pieces were weighed on a precision balance, and the swelling degree (right ear piece weight-left ear piece weight) and swelling inhibition rate (right ear piece weight-left ear piece weight)/left ear piece weight×100%) were calculated.

1.4 Carrageenan-Induced Rat Paw Swelling Test

Eighteen healthy adult male mice were randomly divided into 3 groups. FAPM (100 mg/kg) was administered intraperitoneally once a day for 3 consecutive days. The control group was injected with the same amount of solvent, and the positive drug dexamethasone (4 mg/kg) was administered intragastrically once a day for 3 consecutive days. Thirty minutes after the last administration, 0.1 mL of 1% carrageenan was injected subcutaneously into the right hind paw of each rat, and the plantar thickness was measured before injection and 1, 2 and 3 hours after injection. Three hours later, the rats were sacrificed by dislocation. The feet were cut off from the knee joints and weighed on a precision balance. The swelling degree of the paw (right foot weight-left foot weight) was calculated.

1.5 Statistical Treatment

All experimental data were expressed as "x±s", and SAS software was used to conduct single-factor multi-level T test for statistical analysis.

2. Results

Inflammation is an important defense mechanism produced by the body against harmful stimulation. Inflammation reaction is the most fundamental anti-injury reaction of the body. Inflammation helps to promote wound healing, but it can also cause many injuries, such as arthritis, asthma and body disorders. Inflammation can be divided into infectious inflammation, aseptic inflammation (nonspecific inflammation) and allergic inflammation according to pathogenesis. Xylene-induced mouse ear swelling test and carrageenan-induced rat paw swelling test are the most commonly used methods for evaluating and screening anti-inflammatory drugs. As shown in Tables 10 to 12, intraperitoneal administration of 100 mg/kg FAPM significantly inhibited xylene-induced mouse ear swelling and carrageenan-induced rat paw swelling, and there were statistical differences compared with the control groups. Though the ear swelling degree of the positive drug indomethacin (10 mg/Kg) group was lower than that of the control group, there was no statistical difference. The positive drug dexamethasone (4 mg/kg) significantly inhibited carrageenan-induced rat paw swelling, and its curative effect is slightly better than FAPM.

TABLE 10

Inhibitory Effect of Intraperitoneal Administration of FAPM on Xylene-induced Mouse Ear Swelling Test

| | Dosage | Number of animals | Ear swelling (mg) |
|---|---|---|---|
| Solvent control group | 0.2 ml | 10 | 14.18 ± 1.53 |
| Indomethacin group | 10 mg/Kg | 10 | 12 ± 3.74 |
| FAPM | 100 mg/Kg | 10 | 7.83 ± 3.85** |

Compare with control group **$P < 0.01$.

TABLE 11

Influence of Intraperitoneal Administration of FAPM on Carrageenan-induced Rat Paw Swelling Thickness

| | Dosage | Number of animals | 1 h (mm) | 2 h (mm) | 3 h (mm) |
|---|---|---|---|---|---|
| Solvent control group | 0.2 ml | 6 | 6.09 ± 0.09 | 6.87 ± 0.4 | 7.16 ± 0.67 |
| Indomethacin group | 4 mg/Kg | 6 | 5.52 ± 0.39 | 5.65 ± 0.39** | 6.11 ± 0.15 |
| FAPM | 100 mg/Kg | 6 | 5.72 ± 0.29 | 5.92 ± 0.19** | 6.24 ± 0.20 |

Compare with control group **$P < 0.01$.

TABLE 12

Inhibitory Effect of Intraperitoneal Administration of FAPM on Carrageenan-induced Rat Paw Swelling

|  | Dosage | Number of animals | Paw swelling (g) |
|---|---|---|---|
| Solvent control group | 0.2 ml | 6 | 1.441 ± 0.28 |
| Indomethacin group | 4 mg/Kg | 6 | 0.518 ± 0.05** |
| FAPM | 100 mg/Kg | 6 | 0.834 ± 0.32** |

Compare with control group **$P < 0.01$.

The invention claimed is:

1. A method of treating a smooth muscle spasm-related disease in a subject, comprising administering a therapeutically effective amount of an inhibitor of the cytochrome bc1 complex to the subject, wherein the inhibitor of the cytochrome bc1 complex is atovaquone or a pharmaceutically acceptable salt thereof, and wherein the smooth muscle spasm-related disease is dysmenorrhea.

2. The method according to claim 1, wherein the subject has pain.

3. The method according to claim 1, wherein the subject is a human being.

4. The method according to claim 1, wherein the subject is an animal.

5. The method according to claim 1, wherein atovaquone is administered intraperitoneally.

6. The method according to claim 1, wherein atovaquone is administered intragastrically.

* * * * *